US012588689B2

(12) United States Patent
Kim et al.

(10) Patent No.: US 12,588,689 B2
(45) Date of Patent: Mar. 31, 2026

(54) FEED ADDITIVE COMPOSITION CONTAINING ERYTHRITOL

(71) Applicant: EASY BIO, INC, Seoul (KR)

(72) Inventors: Yong Ho Kim, Cheonan-si (KR); Sang Kyoon Lee, Cheonan-si (KR); Nam Hee Kim, Cheonan-si (KR); Kwan Hu Kim, Cheonan-si (KR)

(73) Assignee: EASY BIO, INC, Seoul (KR)

( * ) Notice: Subject to any disclaimer, the term of this patent is extended or adjusted under 35 U.S.C. 154(b) by 236 days.

(21) Appl. No.: 18/023,208

(22) PCT Filed: Sep. 7, 2021

(86) PCT No.: PCT/KR2021/012152
§ 371 (c)(1),
(2) Date: Feb. 24, 2023

(87) PCT Pub. No.: WO2022/050821
PCT Pub. Date: Mar. 10, 2022

(65) Prior Publication Data
US 2023/0309580 A1     Oct. 5, 2023

(30) Foreign Application Priority Data

Sep. 7, 2020    (KR) ......................... 10-2020-0114074

(51) Int. Cl.

| | |
|---|---|
| *A23K 10/16* | (2016.01) |
| *A23K 20/163* | (2016.01) |
| *A61K 31/047* | (2006.01) |
| *A61K 31/662* | (2006.01) |
| *A61K 31/716* | (2006.01) |
| *C12N 1/16* | (2026.01) |

(52) U.S. Cl.
CPC ............ *A23K 20/163* (2016.05); *A23K 10/16* (2016.05); *A61K 31/047* (2013.01); *A61K 31/662* (2013.01); *A61K 31/716* (2013.01); *C12N 1/16* (2013.01)

(58) Field of Classification Search
CPC ...... A23K 20/163; A23K 10/16; A23K 20/10; A61K 31/047; A61K 31/662; A61K 31/716; C12N 1/16; C12N 1/165; C12R 2001/645; C12R 2001/72
See application file for complete search history.

(56) References Cited

U.S. PATENT DOCUMENTS

| | | | |
|---|---|---|---|
| 5,902,739 A | 5/1999 | Abe et al. | |
| 8,465,761 B2 * | 6/2013 | Navarro ............... | A23K 20/111 |
| | | | 424/93.51 |
| 2015/0272167 A1 | 10/2015 | Varner et al. | |
| 2020/0138735 A1 | 5/2020 | Miller et al. | |

FOREIGN PATENT DOCUMENTS

| | | | | |
|---|---|---|---|---|
| CN | 101790305 A | 7/2010 | | |
| CN | 111363759 A | * 7/2020 | ........... | C12N 15/815 |
| CN | 111990461 A | * 11/2020 | ............. | A23C 9/156 |
| JP | H09-154590 A | 6/1997 | | |
| KR | 10-2004-0019382 A | 3/2004 | | |
| KR | 10-0491165 B1 | 5/2005 | | |
| KR | 10-0767974 B1 | 10/2007 | | |
| KR | 10-0848182 B1 | 7/2008 | | |
| KR | 10-0854567 B1 | 8/2008 | | |
| KR | 10-2010-0109206 A | 10/2010 | | |
| KR | 10-1028476 B1 | 4/2011 | | |
| KR | 10-1417905 B1 | 7/2014 | | |
| KR | 10-1888533 B1 | 8/2018 | | |
| KR | 10-2019-0052072 A | 5/2019 | | |
| KR | 10-2019-0076691 A | 7/2019 | | |

OTHER PUBLICATIONS

Effect of Lysophospholipids Supplementation on Growth Performance, Nutrient Digestibility, Blood Profiles and Carcass Traits in Broilers. Doctoral dissertation, 2014. (Year: 2014).*
International Search Report for PCT/KR2021/012152 mailed Dec. 17, 2021 from Korean Intellectual Property Office.
Xiao Xiangqian, "How to select yeast products under heat stress in dairy cows", Angel Blog, Jun. 10, 2019, URL: https://en.angelyeast.com/blog/animal-nutrition/yeast-products-heat-stress-dairy.html.
Korean Office Action for related KR Application No. 10-2021-0113290 mailed Nov. 22, 2023 from Korean Intellectual Property Office.
Korean Office Action for related KR Application No. 10-2021-0113290 mailed Jul. 21, 2024 from Korean Intellectual Property Office.
Baek Kyung-Hyun et al., "Kemin Korea, contributing to human health with eco-friendly products based on farm verification data", Pig & Pork Korean Pork, May 31, 2020, pp. 432-437, vol. 389.

* cited by examiner

*Primary Examiner* — Erik Kashnikow
*Assistant Examiner* — Janice Y Silverman
(74) *Attorney, Agent, or Firm* — Paratus Law Group, PLLC

(57) ABSTRACT

There is provided a feed additive composition. The feed additive composition includes one or more selected from beta-glucan and lysophospholipid, and erythritol. One or more selected from 60 to 100 parts by weight of the beta-glucan and 5 to 10 parts by weight of the lysophospholipid are contained with respect to 100 parts by weight of the erythritol. The erythritol comes from a culture medium of a strain producing erythritol.

9 Claims, 6 Drawing Sheets

FIG. 3

FEED ADDITIVE COMPOSITION CONTAINING ERYTHRITOL

CROSS-REFERENCE TO PRIOR APPLICATIONS

This application is a National Stage Patent Application of PCT International Patent Application No. PCT/KR2021/012152 (filed on Sep. 7, 2021) under 35 U.S.C. § 371, which claims priority to Korean Patent Application No. 10-2020-0114074 (filed on Sep. 7, 2020), which are all hereby incorporated by reference in their entirety.

BACKGROUND

The present invention relates to a feed additive composition that is capable of reducing high temperature stress of livestock in high-temperature and high-humidity summer season to thus lower the mortality rate of the livestock, raise the feed intake and weight gain thereof, and enhance the productivity thereof.

Owing to consistently increasing global warming, the Earth's average surface temperature increases quickly year by year, and changes caused by the global warming appear obviously. According to a 2020 heatwave influence report by Korean Environment Institute, a daily record high maximum temperature increases by 1.5° C. for 47 years from 1973 to 2019, and 6. 9 heatwave days increase during the same period of time. In 2018, in specific, a daily record high maximum temperature of 41° C. is first monitored on Hongcheon in August, and the national average heatwave days are 31.5, which updates 31.1 heatwave days in 1994 as existing maximum record, and they increase by three times of normal year average heatwave days of 10.1. The heatwave days caused by climate change are expected to increase to 22 days in the second half of the 21st century.

As heatwaves occur, damages on livestock as well as humans are increasing. Because of the increase of a Temperature-Humidity Index (THI) having an influence on an apparent temperature, the mortality rate of the livestock also increases, and in 2018 where heatwave damages are serious, it is reported in Korea that 5.4 million chickens, one hundred forty thousand ducks, and forty thousand pigs are dead. Even though some of them are not dead, damages on them, which are caused by high temperature stress, have increased. Representative damages of animal species by high temperature stress are as follows.

In the case of pigs, feed intake and weight gain are reduced, and the usability of nutrients is lowered, so that their shipping days are delayed. In the case of chickens, they are weak on high temperature the most because their sweat glands are not developed well, thereby causing a high mortality rate, and further, various indirect damages such as feed intake and weight gain decrease, egg shell quality deterioration, fertilization rate reduction, and early embryonic death increase may happen. In the case of cattle as ruminants, in high-temperature breeding environments, they have a body temperature increase, mobility reduction owing to a fermented heat increase of the rumen, and a stay time increase of the feed in the rumen, and their dry matter intake decreases by 6 to 30% according to a report. In the case of milk cows, accordingly, their lactation function becomes deteriorated to thus decrease total milk yield and quality.

In stockbreeding fields in U.S.A., economic loss caused by high temperature stress is estimated to 1.3 to 2.4 trillion won per year. According to the Ministry of Agriculture, Food and Rural Affairs in Korea, the livestock death loss caused by heatwaves is over about 11.8 billion per year, which increases by about 1.8 times year by year, and accordingly, there is a definite need to build a plan for the damage.

To reduce high temperature stress, the number of animals appropriate for breeding has to be kept during their breeding, thereby preventing concentrated breeding, and further, there is a need to build an environmental strategy through which external heat and the heat generated from the body are removed through ventilating and blowing fans. However, the control in environmental elements has an influence on space efficiency or profitability such as the rise in electricity rates, and further, there is a need to take nutritional approach using feed or feed additives capable of controlling generation of metabolic heat, suppressing a body temperature from increasing, enhancing immunity, and releasing high temperature stress.

Many studies to reduce high temperature stress using feed additives have been made, which are disclosed in Korean Patent No. 10-0491165 (entitled 'Additive for milk cow for high temperature stress reduction), Korean Patent No. 10-1417905 (entitled 'Feed additive for high temperature stress reduction of ruminant through fermented heat adjustment of the rumen and feed mixed with feed additive), Korean Patent No. 10-1888533 (entitled 'Animal feed additive composition for high temperature stress reduction, containing *Angelica gigas* root extract), and Korean Patent Application Laid-open No. 10-2019-0076691 (entitled 'Feed additive for high temperature stress reduction, containing *Saccharomyces boulardii*). Most of the effective components of currently used high temperature stress reducing agents are plant extracts, vitamins, minerals, and the like, and with such simple combinations, there is a limitation in effectively reducing the high temperature stress. Therefore, there is a need to develop a feed additive capable of effectively reducing high temperature stress.

On the other hand, erythritol is a four-carbon sugar alcohol and present in mushrooms or fermented foods such as wine, rice wine, soy sauce, and the like. It contains about 70% of the sweetness, has virtually zero calories, and serves as an antioxidant with the ability of excellently removing reactive oxygen species according to reports. When erythritol is dissolved, heat of solution, which absorbs thermal energy, is generated highly so that the erythritol is used for beverage or gum (as disclosed in Korean Patent No. 10-0848182) giving refreshing feeling to the mouth, cold fibers (as disclosed in Korean Patent No. 10-1028476) for providing cold effects in response to water of skin, and cosmetics (as disclosed in Korean Patent No. 10-0767974) such as a mask sheet and cleanser. Like this, erythritol has cold effects in vitro, but it is not known whether upon erythritol intake, it is effective in lowering a body temperature or reducing high temperature stress.

Beta-glucan (β-glucan) is a polysaccharide occurring in the cell walls of yeast, mushrooms, cereals, and the like and serves as an inducer of cytokine when enters a body, thereby activating immune functions to provide anti-cancer, antibacterial, and anti-oxidative effects. In addition, it is reported that it shows excellent blood glucose-lowering effects and blood cholesterol level reduction effects and is effective in improving lipid metabolism.

Lysophospholipid is a phospholipid in which one fatty acid has been cleaved by phospholipase. It is very stable and has surface active properties, so that it is used as an emulsifier for food or cosmetics. It is present naturally in cell membranes, the yolks, white rice, and the like and accelerates the absorption of nutrients through fluidity increase of cell membranes, activation of protein channels, and permittivity increases of cell membranes, so that it can be used as a feed additive to thus improve growth performance.

Until now, however, there are no studies on high temperature stress reduction using the materials as well as the erythritol.

SUMMARY

Accordingly, the present invention has been made in view of the above-mentioned problems occurring in the related art, and it is an object of the present invention to provide a feed additive that is capable of being applied to livestock or fish to thus improve the productivity of the livestock or fish and effectively reducing high temperature stress of the livestock or fish living in their farm in high-temperature and high-humidity summer season.

It is another object of the present invention to provide a feed composition containing the feed additive as mentioned above.

To accomplish the above-mentioned objects, according to the present invention, a feed additive composition may include: one or more selected from beta-glucan and lyso-phospholipid; and erythritol.

As appreciated from an embodiment of the present invention as will be discussed later, in the case where only erythritol is fed, the feed intake increases, and the feed conversion ratio decreases, which are not significant. However, in the case where one or more of beta-glucan and lysophospholipid are added to erythritol, the feed intake and the weight gain are all increased, and the feed conversion ratio and the mortality rate are all lowered, thereby improving productivity. The productivity improvement is remarkably obtained in high-temperature and high-humidity environments.

Further, 50 to 500 parts by weight of beta-glucan and 1 to parts by weight of lysophospholipid are desirably contained with respect to 100 parts by weight of erythritol, and 60 to 100 parts by weight of beta-glucan and 5 to 10 parts by weight of the lysophospholipid are more desirably contained, which are in the specification test range in the embodiment of the present invention as will be discussed later. In the embodiment of the present invention as will be discussed later, synergistic productivity effectiveness is provided in the range of the above-mentioned mixing ratios, but it may be deviated from the range. However, if amounts added are smaller than the above values, it is hard to obtain substantial effectiveness, and contrarily, if amounts added are larger than the above values, the erythritol content is relatively decreased to cause high temperature stress reduction effectiveness to become bad. Therefore, it is desirable that mixing has to be performed within the above range.

In the composition of the present invention, further, erythritol may be used as erythritol being in an isolated state or as erythritol isolated from a culture medium of a strain producing erythritol. Further, the culture medium of the strain may be dried or processed, while being not purely purified, so as to enhance the erythritol content. The strain producing the erythritol is *Yarrowia lipolytica, Candida magnolia, Aureobasidium pullulans, Pseudozyma tsukubaensis,* or *Candida sorbosivorans.* In specific, *Yarrowia lipolytica* EasyYL-01, which is isolated from a marine sample by the inventors has remarkably excellent ability of producing erythritol than other strains. Accordingly, the *Yarrowia lipolytica* EasyYL-01 has been deposited with an accession number KACC83031BP on the microorganisms bank of National Institute of Agricultural Sciences as International Depositary Authority on Jul. 24, 2020.

As appreciated from the embodiment of the present invention as will be discussed later, if the *Yarrowia lipolytica* EasyYL-01 (hereinafter, referred to as 'EasyYL-01') contains glycerol as a carbon source in a medium, it produces erythritol, while having more excellent ability of producing erythritol when compared with other strains. Of course, it is possible that the ability of producing erythritol is optimized according to culture medium compositions and culture conditions.

As appreciated from the embodiment of the present invention as will be discussed later, it is checked that EasyYL-01 produces erythritol with an excellent yield of 123 g/L·7 days even in mass production. However, because the yield is not an optimized yield, of course, the ability of producing erythritol may be more increased through additional optimization in the yield.

The feed additive composition of the present invention is mixed to 0.01 to 5% of erythritol content therein with formulated feed. If an amount of the feed additive added is too small, high temperature stress reduction effectiveness cannot be sufficiently obtained, and contrarily, if an amount of feed additive added is too large, economical advantages and nutrition supply through the feed may be reduced to thus lower productivity.

The feed additive composition of the present invention may be provided as a separate additive composition, but it is mixed with the feed itself and produced to the form of the feed as a final product. The feed may be usefully used for all mammals with the exception of humans, poultry such as chickens, ducks, geese, and the like, livestock such as cattle, horses, goats, sheeps, pigs, rabbits, and the like, and fish.

According to the present invention, if the composition of the present invention is fed to livestock or fish living in a fish farm or water tank that is weak to high temperature stress in summer season, it can achieve high temperature stress reduction, mortality rate decrease, feed intake and weight gain increases, and improvement of productivity thereof, so that it can be applied usefully to a stockbreeding or aquaculture field.

According to the present invention, it can be checked that feeding erythritol remarkably reduces the mortality rate increasing by high temperature stress.

BRIEF DESCRIPTION OF THE DRAWINGS

FIG. 3 shows pictures taken by a thermal imaging camera for in-vitro thermal reduction effect of erythritol.

DETAILED DESCRIPTION

Figure 1:
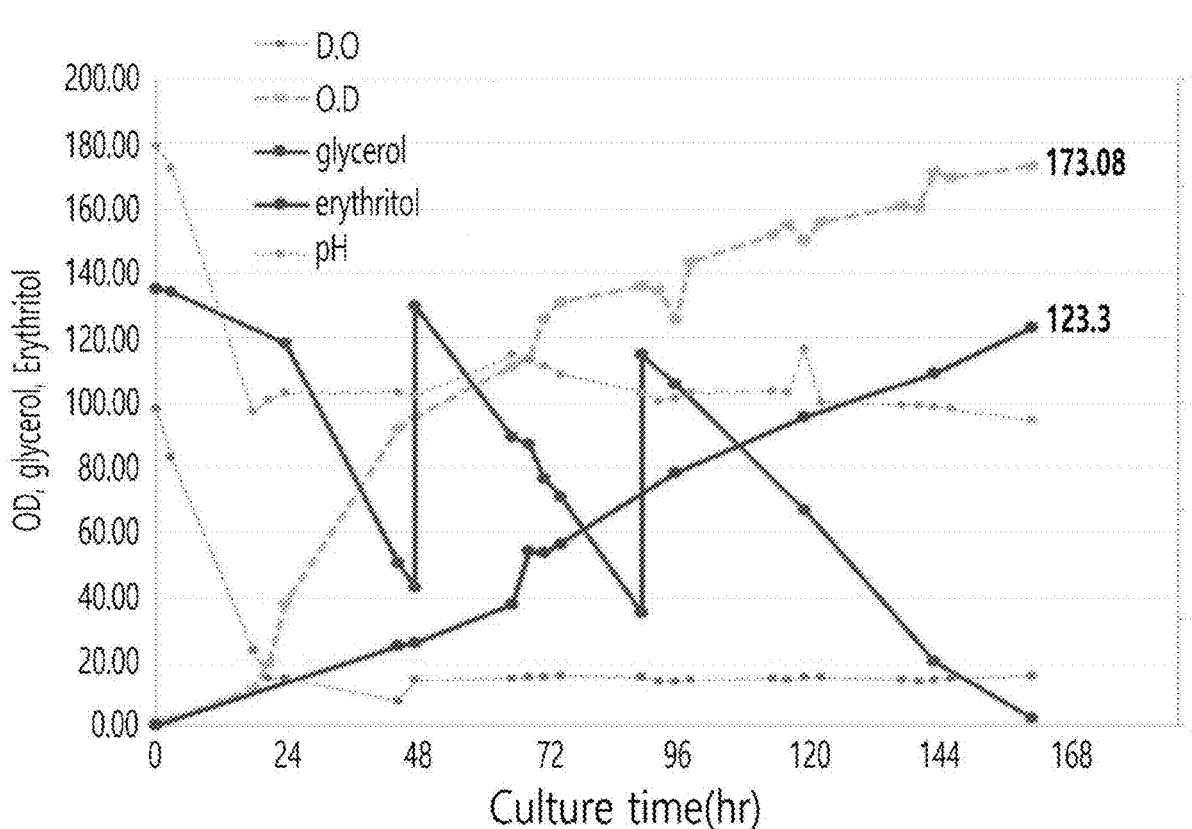
FIG. 1 is a graph showing the growth of a strain in mass production and the ability of producing erythritol.

Hereinafter, an explanation of the present invention will be given in detail. Before the present invention is disclosed and described, it is to be understood that the disclosed embodiments are merely exemplary of the invention, which can be embodied in various forms. Based on the embodiments, those skilled in the art will envision many other possible variations within the scope of the present invention.

EMBODIMENTS

First Embodiment: Comparison of Erythritol Produced by Strains

The most studied strains as strains capable of producing erythritol are *Candida magnolia*, and representative strains industrially used because of high efficiency are *Aureobasidium pullulans* and *Pseudozyma tsukubaensis*. In addition, studies of erythritol production using *Yarrowia lipolytica* or *Candida sorbosivorans* are made.

Basic medium compositions for these four kinds of strains that are adequate for the production of erythritol are determined through pre-tests, and they are listed in Table 1. The *Candida magnolia, Aureobasidium pullulans, Pseudozyma tsukubaensis*, and *Yarrowia lipolytica* were received from Korean Culture Center of Microorganisms (KCCM) and Korean Collection for Type Cultures (KCTC), and tests were carried out with them. In the case of *Yarrowia lipolytica* EasyYL-01, a marine sample acquired by the inventors was cultured in a high-concentration medium, isolated, and prepared. As the results of the pre-tests, *Yarrowia lipolytica* did not produce erythritol when it was cultured with glucose as a carbon source, and the other strains did not produce erythritol when they were cultured with glycerol as a carbon source.

TABLE 1

| | Carbon source (g/L) | | Nitrogen source (g/L) | | | Inorganic fertilizer (g/L) | |
| | | | Yeast | Malt | | | |
| | Glucose | Glycerol | extract | extract | Peptone | $KH_2PO_4$ | $MgSO_4$ |
|---|---|---|---|---|---|---|---|
| *Yarrowia lipolytica* | — | 100 | 1 | — | — | 0.22 | 1 |
| *Candida magnolia* | 100 | — | 5 | — | — | 5 | 0.4 |
| *Aureobasidium pullulans* | 100 | — | 20 | — | 20 | — | — |
| *Pseudozyma tsukubaensis* | 100 | — | 20 | — | — | — | 1 |

The strains were inoculated on the culture media as listed in Table 1 and cultured at a temperature of 30° C. for 72 hours, and after that, supernatant was acquired to quantify erythritol content in a culture medium. The conditions for HLPC analysis are suggested in Table 2, and the amount of erythritol in the culture medium by strain is listed in Table 3.

TABLE 2

| Column | Agilent ZORBAX NH2 (4.6*250 mm, 5 μm) |
|---|---|
| temperature | 35° C. |
| mobile phase | acetonitrile (75): Water(25) |
| flow rate | 1 mL/min |
| Detector | RI detector |
| injection volume | 20 μL |

TABLE 3

| Strain | Erythritol (g/L) |
|---|---|
| *Yarrowia lipolytica* | 1.1 |
| *Yarrowia lipolytica EasyYL-01* | 8.6 |

TABLE 3-continued

| Strain | Erythritol (g/L) |
|---|---|
| *Candida magnolia* | 0.4~0.53 |
| *Aureobasidium pullulans* | 0 |
| *Pseudozyma tsukubaensis* | 1.14 |

Second Embodiment: Production of Erythritol Using EasyYL-01

The culture in a 3,000 L reactor was performed using *Yarrowia lipolytica* Easy YL-01 (hereinafter, referred to as 'EasyYL-01') that was remarkable in production efficacy for erythritol in the first embodiment of the present invention. A culture medium composition is suggested in Table 4, and glycerol was additionally fed to the rate of 100 g/L in 48 and 87 hours of the culture. Reaction pH was controlled to 3, air was fed at 1.5 vvm, and the strain was cultured at 30° C. and 100 rpm for 7 days.

TABLE 4

| Material Name | Amount added (w %) |
|---|---|
| Glycerol | 15 |
| D-glucose | 5 |
| Yeast extract | 0.3 |
| $(NH_4)_2SO_4$ | 0.69 |
| NaCl | 2.65 |
| $KH_2PO_4$ | 0.022 |
| $MgSO_4$ | 0.1 |
| $CuSO_4$ | 0.00025 |

TABLE 4-continued

| Material Name | Amount added (w %) |
|---|---|
| $MnSO_4$ | 0.0025 |
| Emulsifier (span 20) | 0.1 |

FIG. 1 shows the analysis results of the culture medium by culture time, and in this case, erythritol was produced with excellent yield of 123 g/L·7 days even in mass production.

Third Embodiment: Manufacturing a Composition Containing Erythritol

The culture medium containing erythritol produced according to the second embodiment of the present invention was mixed with grain excipients with corn and soybean meal as materials (70 parts by weight of corn and 30 parts by weight of soybean meal) to the ratio of 0.35 to 1, and the mixture was dried to make powder. The erythritol content in the powder ranged from 5 to 6%, and to allow the erythritol content to increase to 20 parts by weight, Zeroe (99% erythritol, Cargill) was added to make a final composition containing erythritol. The water content in the final composition was within 5%.

Fourth Embodiment: In-Vitro Thermal Reduction Effect Check for the Composition Containing Erythritol To check direct thermal reduction effect occurring through endothermic reaction when erythritol was dissolved, the composition containing erythritol produced in the third embodiment of the present invention was put in tepid water, and changes in temperature caused by the dissolution were observed. A term 'mixture powder' used in embodiments as will be discussed below was made by mixing the composition containing erythritol, Lipidol (EASY BIO, 5 to 6% lysophospholipid content), and Biolife (ENT co., Ltd., 40 to 50% beta-glucan content) in the weight ratio 3:1:1.

1) Thermal Reduction Effect Check Through the Measurement of Infrared Thermometer 5 g of composition containing erythritol or mixture powder was put in 100 mL of tepid water with a temperature of 37° C., and next, changes in water temperature was measured using an industrial infrared thermometer (830-T1, Tesco) for five seconds. To perform comparison, a control group using pulverized soybean meal, not the composition containing erythritol was provided, and accordingly, the pulverized soybean meal was put in the same manner above to measure the changes in water temperature.

Figure 2:
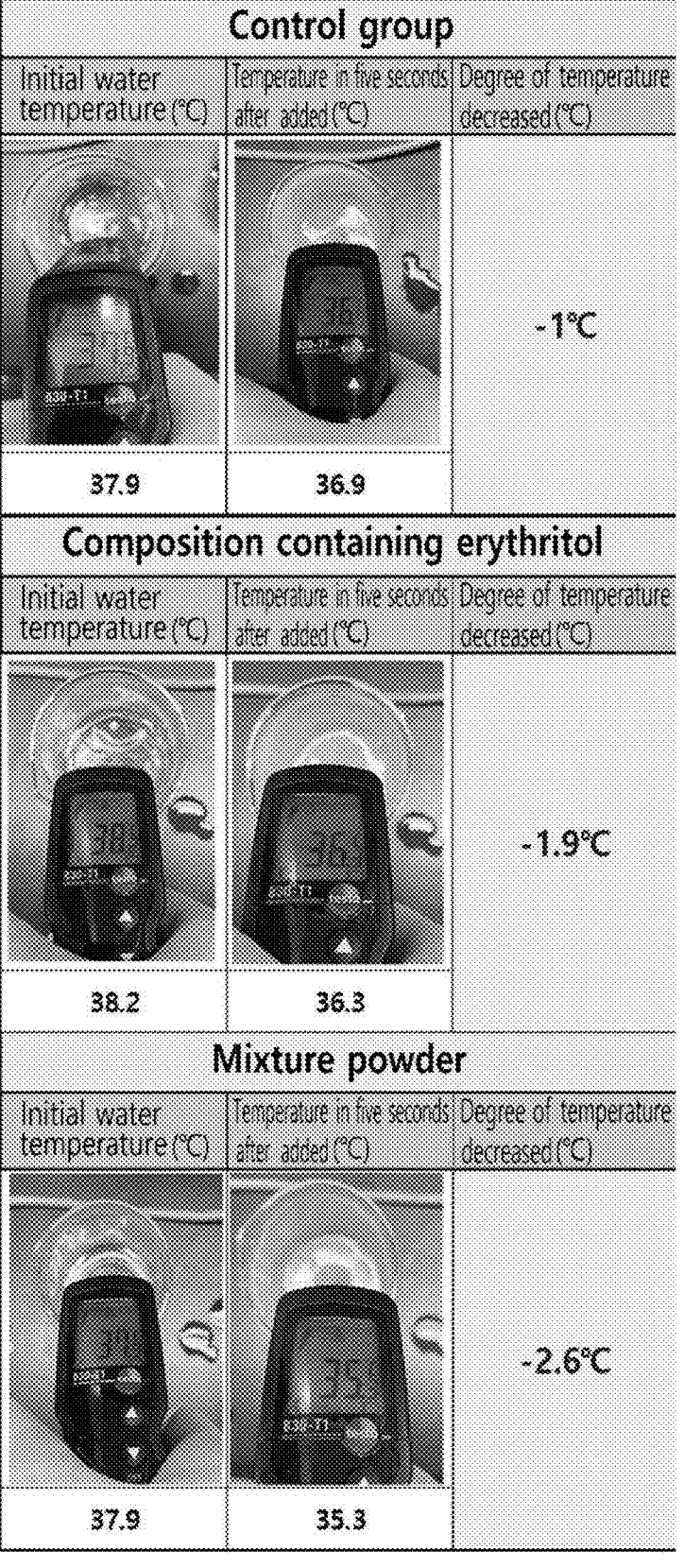
FIG. 2 shows pictures taken by an infrared thermometer for in-vitro thermal reduction effect of erythritol.

As test results, it was checked that the water temperature of 1° C. decreased in the control group, the water temperature of about 1.9° C. decreased in the composition containing erythritol, and the water temperature of about 2.6° C. decreased in the mixture powder (See FIG. 2). It was appreciated that the water temperatures in the composition containing erythritol and the mixture powder decreased more than that in the control group, and further, the thermal reduction effect in the mixture powder made by mixing the composition containing erythritol, beta-glucan, and lysophospholipid was more improved than that in the sole composition containing erythritol.

Figure 3:
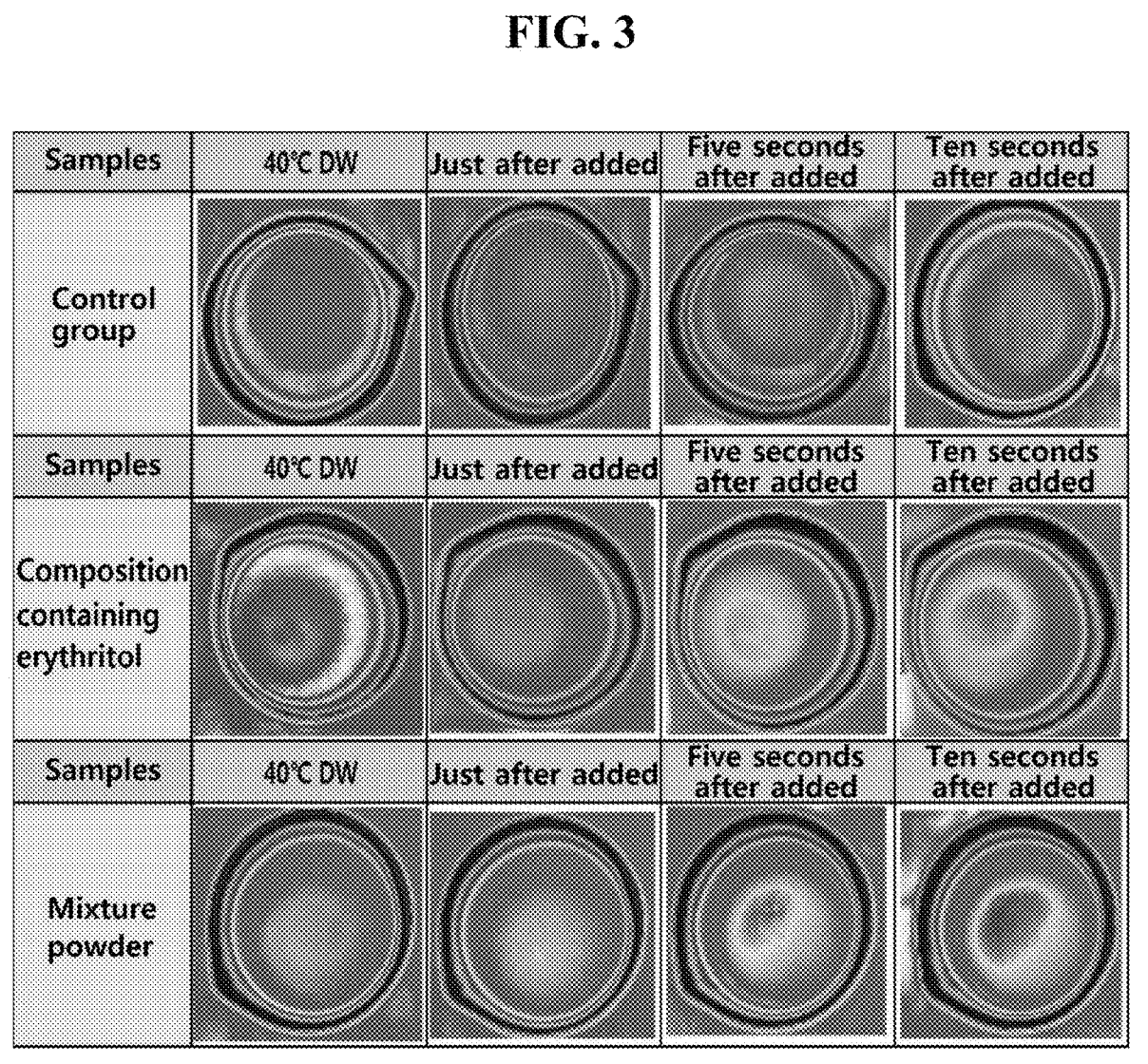

2) Thermal Reduction Effect Check Through Measurement of Thermal Imaging Camera 2.5 g of pulverized soybean meal, composition containing erythritol, or mixture powder was put in 50 mL of tepid water with a temperature of 40° C., and next, changes in water temperature were measured using a thermal imaging camera for ten seconds. FIG. 3 shows the measured results, and it could be checked that the water temperatures became lowered when the composition containing erythritol and the mixture powder were added to the tepid water so that red turned into green. Contrarily, red was reduced in the control group, but green was not observed at all.

Fifth Embodiment: Broiler Chicken Specification Test

1) Composition Containing Erythritol

To investigate the influence of composition containing erythritol on high temperature stress reduction in summer season, 1,280 broiler chickens (Ross 308; male and female chickens) with average weight of 44.0 g and 1 day old were divided into eight treatment groups with 10 repetitions, and then, 16 chickens were arbitrarily located in total 80 fences, thereby performing breeding tests. The feed supplied for the respective treatment groups are as follows, and mixing rates of formulated feed are listed in Table 5. The mixing rates represent weight ratios, and additives by treatment group are post-formulated in a farm. The erythritol (99%) used in the formulation was purchased at Vision Pharmalab Co., Ltd., and the beta-glucan was used with Biolife (ENT Co., Ltd., 40 to 50% beta-glucan content) used in the fourth embodiment of the present invention.

Control group (CON): Formulated feed
E: Formulated feed+0.02% erythritol
B: Formulated feed+0.02% beta-glucan
L: Formulated feed+0.02% lipidol
E+B: Formulated feed+0.02% erythritol+0.02% beta-glucan
E+L: Formulated feed+0.02% erythritol+0.02% lipidol
B+L: Formulated feed+0.02% beta-glucan+0.02% lipidol
E+B+L: Formulated feed+0.02% erythritol+0.02% beta-glucan+0.02% lipidol

TABLE 5

| | Initial period | Starter period | Finisher period |
|---|---|---|---|
| Corn | 57.00 | 61.00 | 63.00 |
| Soybean meal | 26.00 | 23.00 | 19.00 |
| Fermented soybean meal | 5.00 | | |
| Oilseed meal | 2.00 | 6.00 | 8.00 |
| Animal proteins | 2.50 | 4.00 | 4.00 |
| Fats and oils | 2.00 | 2.30 | 2.30 |
| Synthetic amino acids | 1.35 | 1.15 | 1.05 |
| Vitamin premix | 0.20 | 1.13 | 0.11 |
| Mineral premix | 0.15 | 0.12 | 0.12 |
| Enzymes | 0.20 | 0.20 | 0.20 |
| Others | 3.60 | 1.10 | 2.22 |

Figure 4:
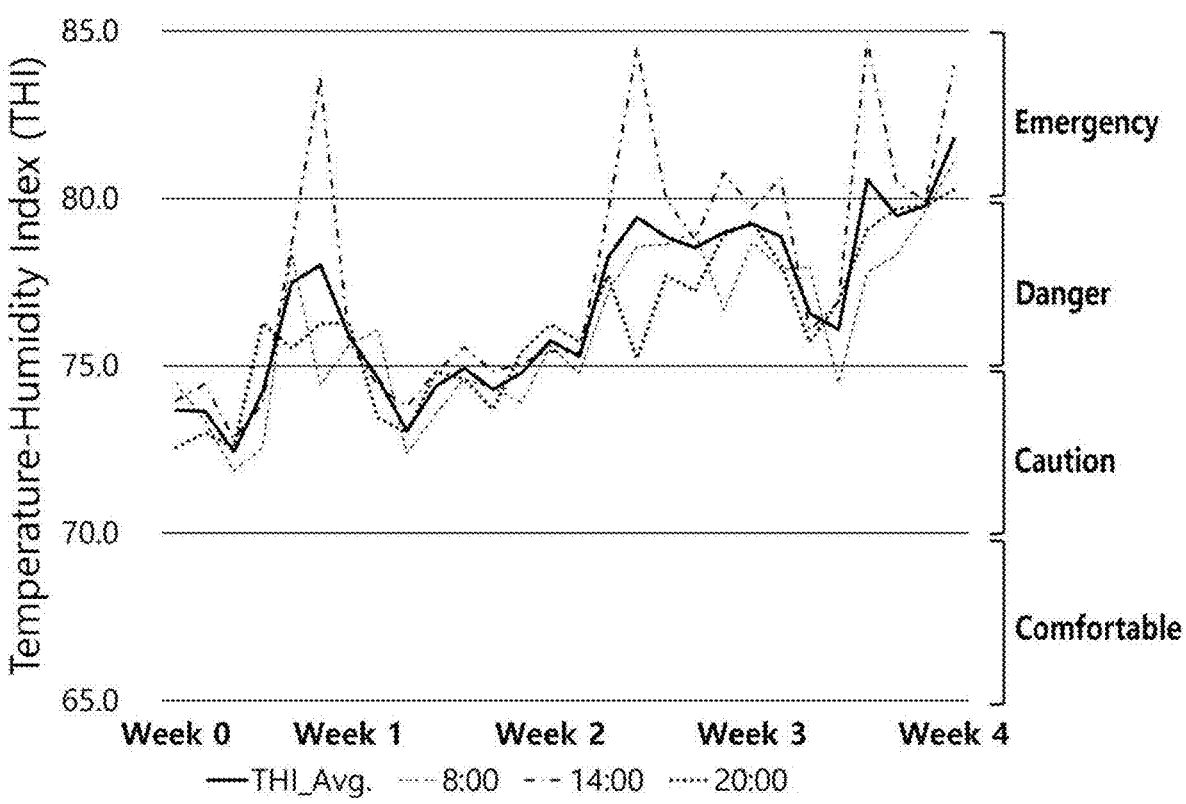
FIG. 4 is a graph showing THI changing according to specification test days of broiler chickens during which erythritol intake is performed.

The feed and water were sufficiently supplied and freely fed. So as to cause stress, 80 to 100 dB noise was produced two times per a day for ten minutes, and to cause high temperature stress, Temperature-Humidity Index (THI) as shown in FIG. 4 was kept.

The weights and feed intake were measured on week 1, week 3, and week 5 to calculate weight gain per day, feed intake per day, and feed conversion ratios (FCR), and the calculated results are listed in Table 6, together with mortality rates.

TABLE 6

| Item | CON | E | B | L | E + B | E + L | B + L | E + B + L | SEM | P-value |
|---|---|---|---|---|---|---|---|---|---|---|
| Initial weight(g) | 43.9 | 44.0 | 44.0 | 44.1 | 44.0 | 44.0 | 44.0 | 44.0 | 0.21 | 1.000 |
| | | | | Step 1(1~7 days of age) | | | | | | |
| Weight(g) | 146.4 | 144.0 | 145.2 | 146.7 | 147.5 | 147.9 | 147.7 | 148.1 | 1.97 | 0.817 |
| Weight gain(g/day) | 14.7 | 14.3 | 14.4 | 14.6 | 14.8 | 14.8 | 14.8 | 14.9 | 0.28 | 0.810 |
| Feed intake(g/day) | 19.0 | 19.4 | 19.0 | 19.2 | 19.6 | 19.7 | 19.6 | 20.6 | 0.91 | 0.951 |
| Feed conversion ratio | 1.31 | 1.36 | 1.33 | 1.31 | 1.33 | 1.33 | 1.33 | 1.39 | 0.065 | 0.989 |
| Mortality rate(%) | 0.0 | 0.0 | 0.0 | 0.0 | 0.0 | 0.0 | 0.0 | 0.0 | — | — |

TABLE 6-continued

| Item | CON | E | B | L | E + B | E + L | B + L | E + B + L | SEM | P-value |
|---|---|---|---|---|---|---|---|---|---|---|
| | | | | Step 2(8~21 days of age) | | | | | | |
| Weight(g) | 712.4$^e$ | 705.4$^e$ | 701.7$^e$ | 727.6$^{de}$ | 755.7$^{bc}$ | 775.4$^{ab}$ | 742.5$^{cd}$ | 796.4$^a$ | 9.83 | <0.01 |
| Weight gain(g/day) | 40.4$^d$ | 40.1$^d$ | 39.8$^d$ | 41.5$^{cd}$ | 43.5$^{bc}$ | 44.8$^{ab}$ | 42.5$^c$ | 46.3$^a$ | 0.72 | <0.01 |
| Feed intake(g/day) | 67.1 | 69.3 | 67.2 | 68.6 | 70.5 | 69.2 | 69.6 | 69.6 | 0.88 | 0.097 |
| Feed conversion ratio | 1.67$^{ab}$ | 1.74$^a$ | 1.70$^{ab}$ | 1.66$^{ab}$ | 1.63$^{bc}$ | 1.54$^{cd}$ | 1.64$^{bc}$ | 1.51$^d$ | 0.04 | <0.01 |
| Mortality rate(%) | 1.3 | 1.3 | 0.0 | 1.9 | 1.9 | 0.6 | 0.0 | 0.0 | 0.68 | 0.191 |
| | | | | Step 3(22~35 days of age) | | | | | | |
| Weight(g) | 1595.3$^e$ | 1592.3$^e$ | 1615.7$^{de}$ | 1649.7$^{cd}$ | 1677.2$^c$ | 1723.3$^b$ | 1661.3$^{bc}$ | 1774.2$^a$ | 15.87 | <0.01 |
| Weight gain(g/day) | 126.1$^c$ | 126.7$^c$ | 130.6$^{bc}$ | 131.7$^{bc}$ | 131.6$^{bc}$ | 135.4$^{ab}$ | 131.3$^{bc}$ | 139.7$^a$ | 2.30 | <0.01 |
| Feed intake(g/day) | 234.6 | 236.9 | 238.5 | 237.1 | 241.8 | 237.9 | 243.0 | 247.3 | 3.10 | 0.106 |
| Feed conversion ratio | 1.86 | 1.88 | 1.83 | 1.80 | 1.84 | 1.76 | 1.86 | 1.77 | 0.04 | 0.233 |
| Mortality rate(%) | 4.4 | 3.8 | 3.8 | 3.1 | 2.5 | 2.5 | 5.6 | 2.5 | 1.30 | 0.628 |
| | | | | Total(1~35 days of age) | | | | | | |
| Weight gain(g/day) | 55.4$^e$ | 55.3$^e$ | 56.1$^{de}$ | 57.3$^{cd}$ | 58.3$^c$ | 60.0$^b$ | 57.8$^c$ | 61.8$^a$ | 0.57 | <0.01 |
| Feed intake(g/day) | 97.0$^c$ | 98.6$^{bc}$ | 98.0$^c$ | 98.3$^{bc}$ | 100.6$^{ab}$ | 99.0$^{bc}$ | 100.4$^{ab}$ | 101.8$^a$ | 0.84 | <0.01 |
| Feed conversion ratio | 1.75$^{ab}$ | 1.79$^a$ | 1.75$^{ab}$ | 1.72$^b$ | 1.73$^b$ | 1.65$^c$ | 1.74$^{ab}$ | 1.65$^c$ | 0.02 | <0.01 |
| Survival rate(%) | 94.4 | 95.0 | 96.3 | 95.0 | 95.6 | 96.9 | 94.4 | 97.5 | 1.24 | 0.535 |

At the results of the entire breeding period as listed in Table 6, there was no significant difference between the weight gain, the feed intake, and the feed conversion ratios of the formulated feed mixed only with erythritol or beta-glucan and those of the formulated feed of the control group. Contrarily, the weight gain in the group having the formulated feed mixed only with lipidol significantly increased when compared with that in the control group. Further, the weight gain, the feed intake, and the feed conversion ratios in the group having the formulated feed mixed with erythritol and beta-glucan or lipidol significantly increased when compared with those in the control group, and in specific, the group having the formulated feed mixed with erythritol and lipidol was greatly reduced in feed conversion ratio when compared with the control group. Further, the group having the formulated feed mixed with erythritol and lipidol was reduced in mortality rate when compared with the control group, thereby resulting in the improvement of a survival rate. The weight gain and the feed intake in the group having the formulated feed mixed with beta-glucan and lipidol were increased when compared with those in the control group, but the feed conversion ratio or the survival rate thereof was similar to that in the control group. The weight gain, the feed intake, and the feed conversion ratio in the group having the formulated feed mixed with all of the erythritol, beta-glucan, and lipidol were remarkably improved when compared with those in the control group. In specific, the group had the weight gain increasing more by about 12%, the feed intake increasing more by 5%, the feed conversion ratio decreasing more by 6%, and the mortality rate decreasing more by 50% than the control group, so that the group showed excellent specification results under the stress conditions. The effectiveness was remarkable at steps 2 and 3 in the growing period where the THI was more dangerous than step 1.

2) Composition Containing Erythritol Culture Medium

Figure 5:
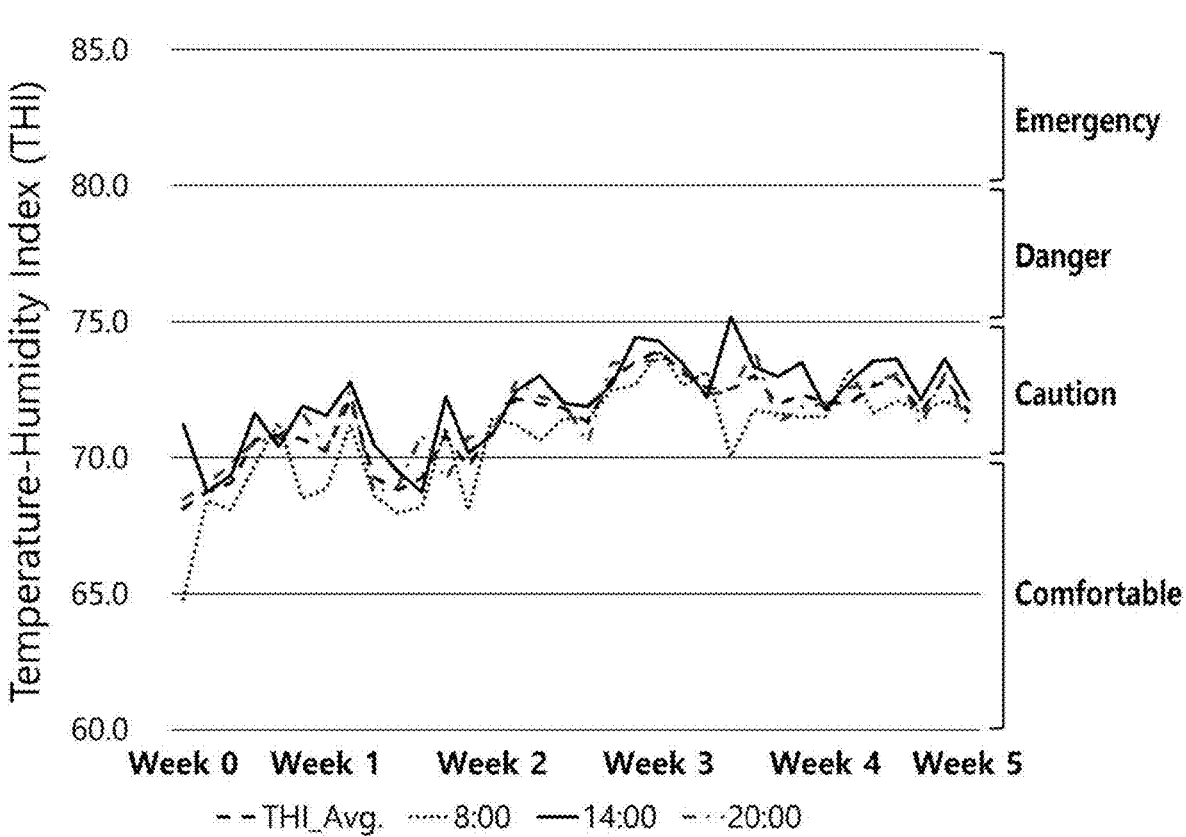
FIG. 5 is a graph showing THI changing according to specification test days of broiler chickens during which erythritol culture medium intake is performed.
Figure 6:
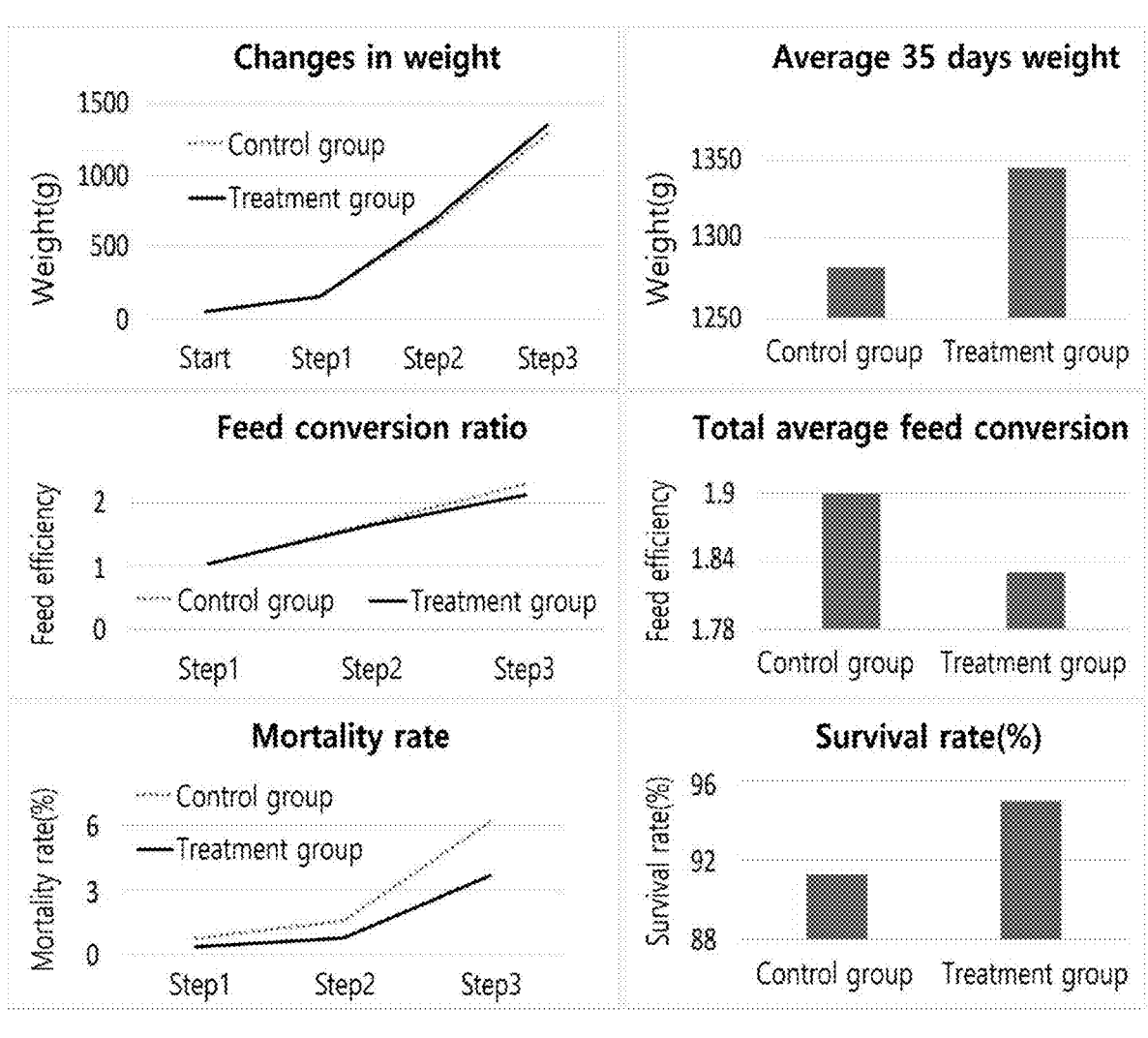
FIG. 6 is a graph showing weight gain, feed conversion ratios, and mortality rates by specification test period of broiler chickens.

To investigate the influence of the composition containing erythritol culture medium on high temperature stress reduction in summer season, 480 broiler chickens (Ross 308; male and female chickens) with 1 day old were divided into two treatment groups with six repetitions, and then, they were arbitrarily located to perform breeding tests. The formulated feed having the formulation as listed in Table 5 were given to the control group, and the formulated feed to which 1 parts by weight of the mixture powder used in the fifth embodiment of the present invention was mixed were given to the test group. The feed and water were sufficiently supplied and freely fed. So as to cause stress, 80 to 100 dB noise was produced for ten minutes a day, and to cause high temperature stress, 70 to 80 THI as shown in FIG. 5 was kept.

The weights and feed intake were measured on week 1, week 3, and week 5 to calculate weight gain per day, feed intake per day, and feed conversion ratios (FCR), and the calculated results are listed in Table 7, together with mortality rates. Further, FIG. 5 shows weight gain, feed conversion ratios, mortality rates, a final average weight gain, a final average feed conversion ratio, and a final survival rate according to a breeding period. As appreciated from Table 7 and FIG. 5, the mortality rate of the test group having the composition of the present invention decreased to about half of the mortality rate of the control group, and the weight gain thereof increased more by 4% than that of the control group.

TABLE 7

| Item | Control group | Treatment group | SEM | P-value |
|---|---|---|---|---|
| Initial weight(g) | 47.3 | 47.3 | 0.06 | 1.0000 |
| Step 1(1~7 days of age) | | | | |
| Weight(g) | 153.5 | 150.3 | 2.29 | 0.3783 |
| Weight gain(g/day) | 17.7 | 17.2 | 0.38 | 0.3968 |
| Feed intake(g/day) | 18.3 | 17.7 | 0.36 | 0.3282 |
| Feed conversion ratio | 1.03 | 1.03 | 0.005 | 0.8220 |
| Mortality rate(%) | 0.8 | 0.4 | 0.29 | 0.3632 |
| Step 2(8~21 days of age) | | | | |
| Weight(g) | 652.6 | 681.3 | 17.30 | 0.2947 |
| Weight gain(g/day) | 33.3 | 35.4 | 1.03 | 0.2039 |
| Feed intake(g/day) | 55.5 | 58.0 | 1.36 | 0.2408 |
| Feed conversion ratio | 1.66 | 1.63 | 0.01 | 0.1119 |
| Mortality rate(%) | 1.6 | 0.8 | 0.57 | 0.3579 |
| Step 3(22~35 days of age) | | | | |
| Weight(g) | 1,281.9 | 1,344.8 | 47.56 | 0.3930 |
| Weight gain(g/day) | 48.4 | 51.0 | 2.55 | 0.5001 |
| Feed intake(g/day) | 101.6 | 104.9 | 3.90 | 0.5717 |
| Feed conversion ratio | 2.29 | 2.12 | 0.077 | 0.1808 |
| Mortality rate(%) | 6.2 | 3.7 | 1.28 | 0.2244 |
| Total (1~35 days of age) | | | | |
| Weight gain(g/day) | 36.3 | 38.2 | 1.39 | 0.3992 |
| Feed intake(g/day) | 66.5 | 68.9 | 2.09 | 0.4684 |

TABLE 7-continued

| Item | Control group | Treatment group | SEM | P-value |
|---|---|---|---|---|
| Feed conversion ratio | 1.90 | 1.83 | 0.026 | 0.1013 |
| Survival rate(%) | $91.3^Y$ | $95.0^K$ | 1.19 | 0.0756 |

The invention claimed is:

1. A feed additive composition consisting of: (1) lysophospholipid and/or beta-glucan; and (2) erythritol.

2. The feed additive composition according to claim 1, wherein 5 to 10 parts by weight of the lysophospholipid are contained with respect to 100 parts by weight of the erythritol.

3. The feed additive composition according to claim 1, wherein the erythritol comes from a culture medium of a strain producing erythritol.

4. The feed additive composition according to claim 3, wherein the strain is *Yarrowia lipolytica, Candida magnolia, Aureobasidium pullulans, Pseudozyma tsukubaensis,* or *Candida sorbosivorans.*

5. The feed additive composition according to claim 4, wherein the strain is *Yarrowia lipolytica* EasyYL-01 (KACC83031BP).

6. The feed additive composition according to claim 5, wherein the culture medium of the strain contains glycerol as a carbon source.

7. A method of reducing high temperature stress in livestock or fish exposed to high temperatures, comprising:
   adding the feed additive of claim 1 to feed, thereby preparing a feedstock; and
   administering the feedstock to the livestock or fish exposed to high temperatures;
   thereby reducing the high temperature stress in the livestock or fish.

8. A feed additive composition consisting of beta-glucan, lysophospholipid, and erythritol.

9. The feed additive composition according to claim 8, wherein 60 to 100 parts by weight of the beta-glucan and 5 to 10 parts by weight of the lysophospholipid are contained with respect to 100 parts by weight of the erythritol.

* * * * *